US007208593B2

(12) United States Patent
Yoshii et al.

(10) Patent No.: US 7,208,593 B2
(45) Date of Patent: Apr. 24, 2007

(54) SELF-CROSS-LINKED ALKYL CELLULOSE

(75) Inventors: Fumio Yoshii, Takasaki (JP); Tamikazu Kume, Takasaki (JP); Tadashi Murakami, Matsudo (JP)

(73) Assignees: Daicel Chemical Industries, Ltd., Osaka (JP); Japan Atomic Energy Research Institute, Tokyo (JP)

( * ) Notice: Subject to any disclaimer, the term of this patent is extended or adjusted under 35 U.S.C. 154(b) by 0 days.

(21) Appl. No.: 11/062,565

(22) Filed: Feb. 23, 2005

(65) Prior Publication Data

US 2005/0148767 A1 Jul. 7, 2005

Related U.S. Application Data

(62) Division of application No. 09/770,634, filed on Jan. 29, 2001, now Pat. No. 6,875,862.

(51) Int. Cl.
*C08B 37/00* (2006.01)
(52) U.S. Cl. .................. 536/99; 536/55.1; 536/56; 536/124; 514/23; 514/25; 514/54; 514/57
(58) Field of Classification Search ............... 536/124, 536/56, 55.1, 99; 514/57, 54, 25, 23
See application file for complete search history.

(56) References Cited

U.S. PATENT DOCUMENTS

| 2,895,891 | A | * | 7/1959 | Miller | .................. | 516/106 |
| 3,898,143 | A | | 8/1975 | Assarsson et al. | ....... | 204/159.2 |
| 4,242,506 | A | | 12/1980 | Schweiger | .................. | 536/59 |

FOREIGN PATENT DOCUMENTS

| JP | 47-17965 | 5/1972 |
| JP | 08-089796 | 4/1996 |
| JP | 08-196901 | 8/1996 |
| JP | 10-324701 | 12/1998 |

OTHER PUBLICATIONS

Leavitt, F.C. Journal of Polymer Science, 1961, 51, 349-357.*
Kume, T. et al J. Appl. Polym. Sci. 2000, 78, 278-283.*
2G05; Radiation Crosslinking of Cellulose Ethers and Its Biodegradability; R.A. Wach, H. Mitomo, Dept. of Biological and Chemical Eng., Faculty of Eng., Gunma University; p. 123.
Development of Radiation Crosslinking Techniques of Biodegrable Polymers; F. Yoshii, R.A. Wach, H. Nagasawa, H. Mitomo and T. Kume; Polymer Preprints, Japan, vol. 49, No. 14 (2000); pp. 4375-4376.
1A07; Radiation Processing of Biodegradable Polymer 3 Crosslinking of Cellulose Ethers At High Concentrated Aqueous Solution; Department of Biological and Chenical Engineering, Gunma University, Takasaki Radiation Chemistry Research Establishment, JAERI; Radoslaw A. Wach, Hiroshi Mitomo, Fumio Yoshii, Tamikazy Kume; pp. 14-15, 58-59, 2000.
Leavitt, C.F. Journal of Polymer Science, 1961, vol. 51, pp. 349-357.
Leavitt, F.C. "Crosslinking of Cellulosics by High Energy Radiation. II." Journal of Polymer Science, 1961, vol. 51, pp. 349-357.
Frederick C. Leavitt, "Crosslinking of Cellulosics by High Energy Radiation II", Journal of Polymer Science, vol. 51, pp. 349-357, 1961.
Wach et al "Radiation Processing of Biodegradable Polymer 3 Cross-linking of cellulose Ethers at High Concentrated aqueous Solutions", 1A07, English Translation, pp. 14-15, 2000.
Wach et al Radiation Processing of Biodegradable Polymer 2 "Hydrogel from Cellulose Derivatives", 1O08, English Translation, pp. 14-15, 1999.
Wach et al "Radiation Cross-linking of Cellulose Ethers and Its Biodegradability", 2G05, Autumn Meeting (2000), English Translation, vol. 55, No. 3, pp. 14-15, 2000.
2G05; Radiation Crosslinking of Cellulose Ethers and Its Biodegradability; R.A. Wach, H. Mitomo, Dept. of Biological and Chemical Eng., Faculty of Eng., Gunma University; pp. 123, 2000.
Development of Radiation Crosslinking Techniques of Biodegrable Polymers; F. Yoshii, R.A. Wach, H. Nagasawa, H. Mitomo and T. Kume; Polymer Preprints, Japan, vol. 49, No. 14 (2000); pp. 4375-4376.
1O 07; Radiation Processing of Biodegradable Polymer 1. Improvement of Processability. F. Yoshii, D. Darwis, K. Nishimura, H. Mitomo, TRCRE, JAERI, Gunma University; pp. 13-16, 1999.

(Continued)

*Primary Examiner*—Shaojia Anna Jiang
*Assistant Examiner*—Ganapathy Krishnan
(74) *Attorney, Agent, or Firm*—Nixon & Vanderhye, P.C.

(57) ABSTRACT

A process for producing a self-cross-linking alkyl cellulose derivative, which includes irradiating, with radioactive rays, a mixture of a starting alkyl cellulose derivative (the number of carbon atoms of the alkyl group is 1 through 3, the alkyl group may be substituted by a hydroxyl group or a carboxyl group, and the carboxyl group may form a salt) (100 parts by weight) and water (5–2,000 parts by weight), and thus obtained self-cross-linking alkyl cellulose derivative has an improved biodegradability and excellent water-absorbability.

15 Claims, 6 Drawing Sheets

OTHER PUBLICATIONS 1A 07; Radiation Processing of Biodegradable Polymer 3 Crosslinking of Cellulose Ethers At High Concentrated Aqueous Solution; Department of Biological and Chenical Engineering, Gunma University, Takasaki Radiation Chemistry Research Establishment, JAERI; Radoslaw A. Wach, Hrioshi Mitomo, Fumio Yoshii, Tamikazy Kume; pp. 14-15, 58-59 (2000).

* cited by examiner

SELF-CROSS-LINKED ALKYL CELLULOSE

This application is a division of U.S. patent application Ser. No. 09/770,634 filed Jan. 29, 2001 (now U.S. Pat. No. 6,875,862), the entire content of which is hereby expressly incorporated hereinto by reference.

BACKGROUND OF THE INVENTION

1. Field of the Invention

The present invention relates to a process for producing a self-cross-linking alkyl cellulose derivative and a self-cross-linking alkyl cellulose derivative further exhibiting biodegradability which are produced by irradiating a mixture of an alkyl cellulose derivative and water with radioactive rays; and a novel self-cross-linking alkyl cellulose derivative produced through the above process.

2. Background Art

Conventionally, carboxymethyl cellulose (CMC) or salts thereof are employed in the form of aqueous compositions such as paints, adhesives, coating agents, cataplasms, and soft cream; in ground-improving agents in the construction field; and in soil-improving agents, water retention agents, and coating agents in the agricultural and horticultural fields.

Japanese Patent Application Laid-Open (kokai) No. 10-324701 discloses carboxypolysaccharides which are produced chemically through intramolecular or intermolecular self-cross-linking of hyaluronic acid, alginic acid, or CMC (the term "self-cross-linking" refers to cross-linking that proceeds in the absence of a cross-linking agent). According to the method described in this publication, carboxyl and hydroxyl groups of carboxypolysaccharides are subjected to intramolecular or intermolecular dehydration in the presence of a catalyst so as to form ester bonds, whereby self-cross-linking is achieved. This method does not employ radioactive rays to effect cross-linking, and therefore, the preparation of raw materials is complex, and a dehydration catalyst is necessary.

Japanese Patent Application Laid-Open (kokai) Nos. 8-89796 and 8-196901 disclose water-absorbable resins which are produced through chemical cross-linking of carboxyalkyl cellulose or carboxyalkyl starch with amino acids. The cross-linking process according to this publication does not employ radioactive rays, and has some disadvantages that the preparation of raw materials is complex and an expensive cross-linking agent is necessary.

In general, water-soluble polymers are cross-linked by use of a cross-linking agent or under irradiation with radioactive rays, and the resultant polymers are used as highly water-absorbable resins or gelation compounds (simply referred to as "gel"). Particularly, polyacrylic acid is employed as absorbing agents in, for example, paper diapers. However, polyacrylic acid is not biodegradable to any significant extent and has, therefore, associated disposal problems. When such water-absorbable resins or gels are intended to be used in the construction field; i.e., outdoors, they must possess biodegradability after use.

CMC, which is a water-soluble polymer, is known to be biodegradable in the presence of an enzyme such as cellulase. However, when CMC alone is exposed to radioactive rays, CMC is decomposed prior to cross-linking thereof, and thus CMC is not effectively cross-linked through the irradiation.

Japanese Patent Publication (kokoku) No. 47-17965 discloses that CMC can be reacted with epichlorohydrin, to thereby produce a cross-linked product. However, the resultant product exhibits poor water-absorbability and raises problems in terms of safety.

SUMMARY OF THE INVENTION

In view of the foregoing, the present invention provides a process for producing a self-cross-linking alkyl cellulose derivative through irradiation with radioactive rays; a self-cross-linking alkyl cellulose derivative, a self-cross-linking alkyl cellulose derivative exhibiting improved biodegradability, and a self-cross-linking alkyl cellulose derivative exhibiting excellent water-absorbability produced through the process; and use of the derivatives.

The present inventors have performed extensive studies, and have found that a self-cross-linking alkyl cellulose derivative can be easily produced by irradiating an aqueous solution of an alkyl cellulose derivative such as CMC with radioactive rays; and that a self-cross-linking alkyl cellulose derivative exhibiting biodegradability or excellent water-absorbability, or a self-cross-linking alkyl cellulose derivative exhibiting biodegradability and excellent water-absorbability can be produced by modifying the raw materials or irradiation conditions. The present invention has been accomplished on the basis of these findings.

Accordingly, in a first aspect of the present invention, there is provided a process for producing a self-cross-linking alkyl cellulose derivative, which comprises irradiating, with radioactive rays, a mixture of an alkyl cellulose derivative serving as a starting material (hereinafter the derivative may be referred to simply as a "starting alkyl cellulose derivative") (the number of carbon atoms of the alkyl group is 1 to 3, the alkyl group may be substituted by a hydroxyl group or a carboxyl group, and the carboxyl group may form a salt) (100 parts by weight) and water (5–2,000 parts by weight).

Preferably, the starting alkyl cellulose derivative is carboxyalkyl cellulose, hydroxyalkyl cellulose, or alkyl cellulose, having at least one hydroxyl group or carboxyl group per glucose unit; or a mixture of these celluloses.

Preferably, 20% or more of the entirety of carboxyl groups of the starting alkyl cellulose derivative form an alkali metal salt, an ammonium salt, or an amine salt.

Preferably, the starting alkyl cellulose derivative has an average polymerization degree of 10–2,000 and an average etherification degree of 0.5 or more.

Preferably, the self-cross-linking alkyl cellulose derivative has a gel fraction of 0.1% or more.

Preferably, the irradiation dose of radioactive rays is 0.1 kGy or more as reduced to γ-rays.

Preferably, the produced alkyl cellulose derivative is subjected to an additional step of drying.

In a second aspect of the present invention, there is provided a self-cross-linking alkyl cellulose derivative produced through the aforementioned production process.

Preferably, when the dried self-cross-linking alkyl cellulose derivative (0.2 g) is added to an aqueous acetic acid solution (buffer having a pH of 4.5) (10 ml) containing 0.5 wt. % of cellulase and the resultant solution is allowed to stand at 40° C. for eight hours, the percent biodegradation of the derivative is 50% or more.

Preferably, when the dried self-cross-linking alkyl cellulose derivative (0.2 g) is added to an aqueous acetic acid solution (buffer having a pH of 4.5) (10 ml) containing 0.5 wt. % of cellulase and the resultant solution is allowed to stand at 40° C. for eight hours, the percent biodegradation is 70% or more.

Preferably, the amount of distilled water which the self-cross-linking alkyl cellulose derivative absorbs is 30 times or more the weight of the derivative.

Preferably, the resultant gel has a compressive strength of 100 g/cm² or more.

In a third aspect of the present invention, there is provided a medical product, a cosmetic product, a sanitary product, or an agricultural water retention agent, comprising the aforementioned self-cross-linking-alkyl cellulose derivative.

In a fourth aspect of the present invention, there is provided a chromatography carrier, an industrial material, a ground-improving agent, or a soil-improving agent, comprising the aforementioned self-cross-linking alkyl cellulose derivative.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the accompanying drawings, in which.

DETAILED DESCRIPTION OF PREFERRED EMBODIMENTS

Figure 1:
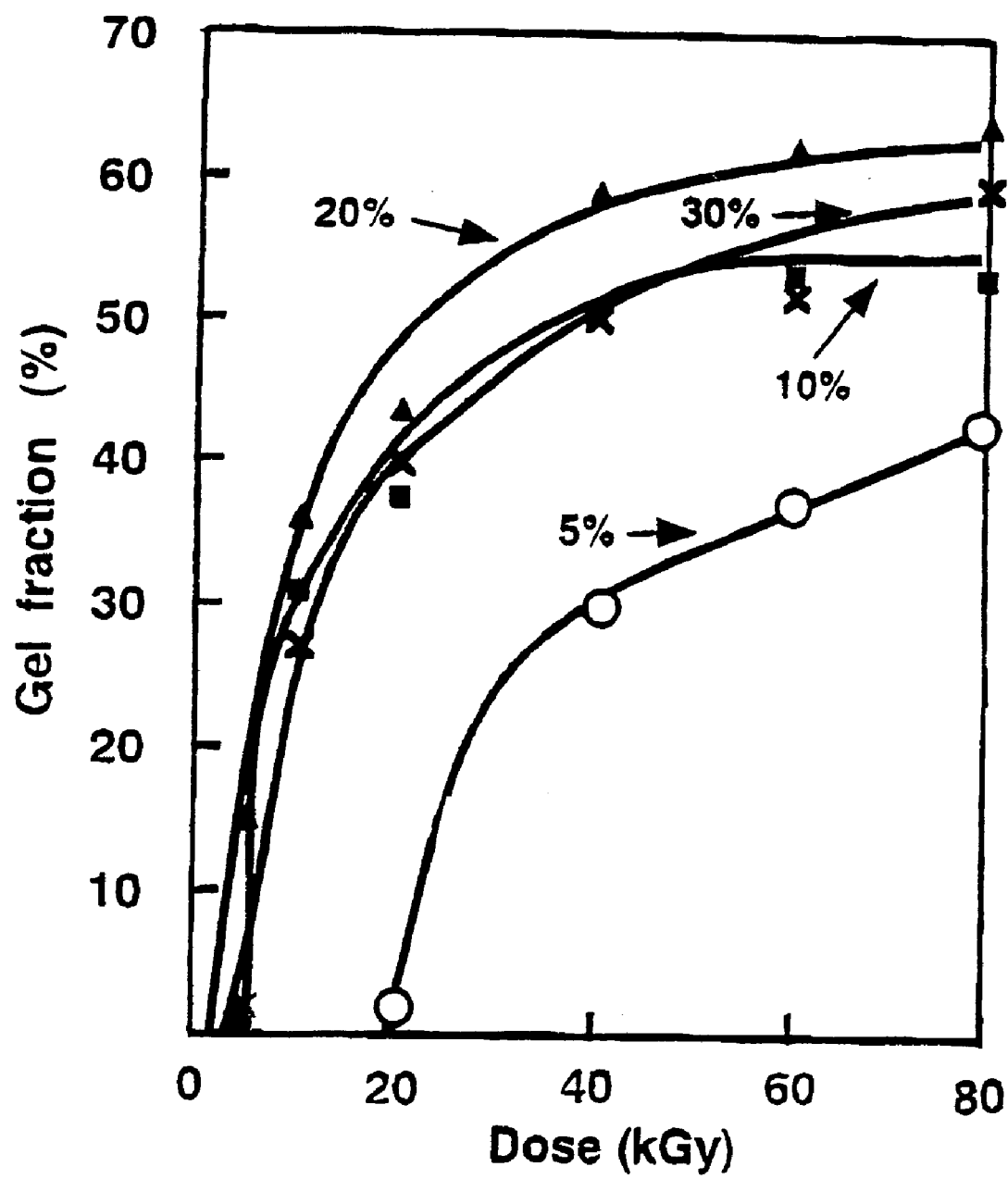
FIG. 1 is a graph obtained from the results of Example 1 and showing the relation between the irradiation dose and the gel fraction.

In the present invention, the alkyl cellulose derivative serving as a starting material is carboxyalkyl cellulose (A), hydroxyalkyl cellulose (B), alkyl cellulose (C), a mixture of these celluloses, or a mixture of at least one of (A), (B) and (C) as a main component with an unmodified cellulose. Each of these celluloses has at least one hydroxyl group or carboxyl group on average per glucose unit.

Carboxyalkyl Cellulose (A)

Carboxyalkyl cellulose (A) serving as a starting material in the present invention is produced by substituting the hydrogen atom of a hydroxyl group in a cellulose molecule by a carboxymethyl group, a carboxyethyl group, or a carboxypropyl group. Carboxyalkyl cellulose (A) is preferably carboxymethyl cellulose or carboxyethyl cellulose.

In the aforementioned carboxyalkyl cellulose, 20% or more, preferably 40% or more, of the entirety of carboxyl groups form an alkali metal salt, an ammonium salt, or an amine salt. Examples of alkali metal salts include a sodium salt, a potassium salt, and a lithium salt. Of these, a sodium salt is preferable.

When the percentage of carboxyl groups which constitute the salt is less than 20%, the cellulose is difficult to be uniformly mixed with water or solved in water. The upper limit for the percentage of carboxyl groups which form the salt is not particularly limited, and may be as high as 100%.

Hydroxyalkyl Cellulose (B)

Hydroxyalkyl cellulose (B) serving as a starting material in the present invention is produced by reacting the hydrogen atom of a hydroxyl group in a cellulose molecule with, for example, ethylene oxide or propylene oxide. Therefore, the hydrogen atom is substituted by a hydroxyethyl group (—$C_2H_4OH$), a hydroxyisopropyl group (—$C_3H_6OH$), or a hydroxy-n-propyl group (—$C_3H_6OH$); or by a polyoxyalkylene ether-substituted group which is formed by reacting thus obtained terminal hydroxyl group with 1 to 10 molecules of ethylene oxide or propylene oxide. Hydroxyalkyl cellulose (B) is preferably hydroxyethyl cellulose (HEC) or hydroxypropyl cellulose (HPC).

Taking HEC as an example, HEC is produced through the following process: cellulose is reacted with ethylene oxide (EO) in the presence of a hydrophilic organic solvent and sodium hydroxide; and subsequently the resultant reaction mixture is subjected to neutralization, purification, drying, and pulverizing, to thereby produce HEC. During the course of hydroxyethylation of cellulose, formed hydroxyethyl groups are further reacted with EO. When the amount of alkali and water during hydroxyethylation is appropriately selected HEC which contains uniformly distributed substituents and exhibits resistance to enzymatic hydrolysis is produced. The amount by mole of EO added to cellulose is represented by "molar substitution" (MS). When MS is 1, the degree of substitution (DS) of cellulose is 0.7. In the case of a commercially available HEC, MS is 1.5–3.0, DS is 0.9–1.4. HEC having an MS of 1 or more (DS: 0.7 or more) is water-soluble.

Alkyl Cellulose (C)

Alkyl cellulose (C) serving as a starting material in the present invention is produced by partially substituting hydrogen atoms of hydroxyl groups in a cellulose molecule with a methyl group, an ethyl group, or a propyl group. Alkyl cellulose (C) is preferably methyl cellulose.

The degree of alkyletherification of the aforementioned alkyl cellulose is 66% or less, preferably 50% or less, more preferably 33% or less.

The average polymerization degree of the aforementioned alkyl cellulose derivative is not particularly limited, but in practice, the degree is about 10–2,000, preferably about 50–1,000, more preferably about 200–800.

The average etherification degree (i.e., the degree to which the hydrogen atom of a hydroxyl group on cellulose is substituted by a carboxyalkyl group, a hydroxyalkyl group, or an alkyl group) of the alkyl cellulose derivative is 0.5 or more, preferably 0.8 or more, more preferably 1.1 or more. The upper limit is 3.

When the average etherification degree is less than 0.5, satisfactory cross-linking does not result.

The alkyl cellulose derivative serving as a starting material in the present invention may be a product produced through a known process, and particularly, commercially available products may be used.

Carboxyalkyl cellulose can be produced through a variety of processes, such as a slurry process (high concentration solution process) or a kneader process (low concentration solution process), which are conventionally employed. For example, carboxyalkyl cellulose can be produced through a process including a mercerization step and a carboxyalkylation step. In the mercerization step, cellulose is reacted with an alkali, to thereby form alkali cellulose. In the carboxyalkylation step, the alkali cellulose resulting from the mercerization step is reacted with monochloroacetic acid, to thereby produce carboxymethyl cellulose; or the alkali cellulose is reacted with an acrylate, and then the resultant ester is subjected to hydrolysis, to thereby produce carboxyethyl cellulose.

Hydroxyalkyl cellulose is produced by reacting a hydroxyl group of cellulose with alkylene oxide. For example, hydroxyethyl cellulose and hydroxypropyl cellulose are produced by reacting hydroxyl groups of cellulose with ethylene oxide and propylene oxide, respectively. Such hydroxyalkyl cellulose may further be reacted with alkylene oxide. For example, ethylhydroxyethyl cellulose is produced by reacting hydroxyethyl cellulose with ethylene oxide.

Alkyl cellulose can be produced through the reaction between alkali cellulose and alkyl chloride or dialkyl sulfate. For example, methyl cellulose is produced through the reaction between alkali cellulose and methyl chloride or dimethyl sulfate; and ethyl cellulose is produced through the reaction between alkali cellulose and ethyl chloride or diethyl sulfate.

Cellulose obtained from a variety of materials such as wood pulp and linter pulp may be employed. The alkali may be an alkali metal such as lithium, potassium, or sodium; ammonia; or amine. Of these, sodium is usually employed in the form of hydroxide or aqueous solution.

The amount of alkali (e.g., sodium hydroxide) which is employed in the mercerization step is usually about 30–80 parts by weight, preferably about 40–75 parts by weight, on the basis of 100 parts by weight of cellulose. The amount of alkali (e.g., sodium hydroxide) which is employed in the slurry process is usually 35–70 parts by weight, preferably about 45–65 parts by weight, on the basis of 100 parts by weight of cellulose. In order to carry out mercerization, cellulose is employed usually in an amount of about 1–7 wt. % and about 10–25 wt. %, in the slurry process and the kneader process, respectively. The amount of alkali employed in the mercerization step in the slurry process differs from the amount of alkali employed in the mercerization step in the kneader process. In the slurry process, mercerization may be carried out in an aqueous medium containing an alkali in an amount of about 1–10 wt. %. In the kneader process, mercerization may be carried out in an aqueous medium containing an alkali in an amount of about 2–15 wt. %.

Mercerization may be carried out in the presence of an appropriate solvent. Examples of such solvents include water; alcohols such as ethanol and isopropanol; ketones such as acetone; and cellosolves such as methyl cellosolve and ethyl cellosolve.

The thus-produced carboxyalkyl cellulose can be purified through moisture-evaporation, washing, and then drying. If necessary, after the reaction is complete, the carboxyalkyl cellulose may be treated with a peroxide such as hydrogen peroxide or peracetic acid to control the viscosity.

In the present invention, a mixture of a starting alkyl cellulose derivative and water, in which the amount of water is 5 to 2,000 parts by weight on the basis of 100 parts by weight of the alkyl cellulose derivative, is irradiated with radioactive rays.

As described above, when a starting alkyl cellulose derivative such as CMC is irradiated with radioactive rays, decomposition of the derivative precedes cross-linking thereof. However, in the presence of water, hydroxy radicals are generated through the irradiation, and cross-linking of the derivative proceeds through the intervention of the hydroxy radicals.

A mixture of the alkyl cellulose derivative and water may assume a form such that the derivative contains water absorbed in its structure, giving rise to a paste or an aqueous solution. Preferably, the alkyl cellulose derivative and water are uniformly mixed.

When the amount of water falls below the above range, the degree of decomposition of the starting alkyl cellulose derivative increases, whereas when the amount of water is in excess of the above range, it is difficult for the derivative to undergo cross-linking.

Examples of water employed in the present invention include city water, industrial water, degassed water, deionized water, gel-filtered water, and distilled water. Preferably, water not containing oxygen or ions is employed.

Examples of the types of radioactive rays employed for irradiation in the present invention include α-rays, β-rays, γ-rays, X-rays, electron beams, and UV-rays. Of these, X-rays, electron beams, or γ-rays from cobalt 60 are preferable. Particularly, irradiation with γ-rays or irradiation with electron beams by use of an electron accelerator can be effectively employed for the formation of a cross-linking structure.

In the present invention, the dose of radioactive rays varies between whether enhancement of water absorbability is intended or enhancement of gel strength is intended. Also, the dose varies in relation to the mixing ratio of the starting alkyl cellulose derivative and water.

In order to enhance water absorbability, the dose of radioactive rays is 0.1–50 kGy, preferably 0.3–20 kGy, more preferably 0.5–10 kGy, as reduced to γ-rays. When the dose falls below the above range, cross-linking of the starting alkyl cellulose derivative does not proceed, and thus the water-absorbability of the resultant resin is unsatisfactory. In contrast, when the dose is in excess of the above range, cross-linking of the derivative is excessive, and thus the water-absorbability of the resultant resin is unsatisfactory.

In order to obtain a high strength of the gel, the dose of radioactive rays is 20–300 kGy, preferably 30–200 kGy, and more preferably 50–100 kGy, as reduced to γ-rays. When the dose falls below the above range, the strength of the resultant gel, particularly compressive strength decreases. In contrast, when the dose is in excess of the above range, production costs increase.

When the alkyl cellulose derivative is irradiated with radioactive rays in the absence of oxygen, the derivative can be cross-linked effectively (i.e., at a low irradiation dose). This is because, when irradiation is carried out in the presence of oxygen, the extent of oxidative decomposition of the derivative increases.

In order to enhance water absorbability, the gel fraction of the above-produced self-cross-linking alkyl cellulose derivative is 0.1–50%, preferably 0.5–40%, more preferably 1–30%. When the gel fraction of the self-cross-linking alkyl cellulose derivative falls below the above range, cross-linking of the derivative is unsatisfactory. In contrast, when the gel fraction is in excess of the above range, cross-linking of the derivative is excessive, and thus the water-absorbability of the resultant resin is unsatisfactory.

In order to obtain a high strength of the gel, the gel fraction of the self-cross-linking alkyl cellulose derivative is 30% or more, preferably 50% or more, more preferably 60% or more. The upper limit of the gel fraction is 100%. When the gel fraction of the derivative falls below the above range, the strength of the resultant gel is unsatisfactory.

The gel fraction is obtained through the following procedure: the self-cross-linking alkyl cellulose derivative is soaked in a large amount of distilled water (e.g., the amount is 10–100 times that of the derivative) for 48 hours; the resultant derivative is subjected to filtration through use of a 20-mesh stainless steel sieve; and the ratio of the insoluble derivative remaining on the sieve is obtained as the gel fraction of the derivative. The gel fraction is obtained from the following formula:

Gel fraction (%)=($W_2/W_1$)×100

(wherein $W_1$ represents the weight of the dried starting alkyl cellulose derivative employed, and $W_2$ represents the weight of the dried insoluble derivative after filtration of the cross-linked derivative).

The biodegradability of the above-produced self-cross-linking alkyl cellulose derivative is measured through the following procedure.

The self-cross-linking alkyl cellulose derivative produced through irradiation with radioactive rays is dried, and the dried derivative (0.2 g) is added to an aqueous acetic acid solution (buffer having a pH of 4.5) (10 ml) containing 0.5 wt. % of cellulase, which is an enzyme employed for testing biodegradability. The resultant solution is allowed to stand at 40° C. for 0 to 8 hours, to thereby permit biodegradation of the derivative. The elapsed time and the percentage of the remaining self-cross-linking alkyl cellulose derivative are measured. The biodegradation (%) is obtained by subtracting the percentage of the remaining derivative from 100%.

In order to enhance water absorbability, the percent biodegradation of the self-cross-linking alkyl cellulose derivative during the above-mentioned period of time is 50% or more, preferably 70% or more, more preferably 80% or more, much more preferably 90% or more. In terms of the time versus percent biodegradation, eight-hour biodegradation desirably attains a percent biodegradation of 50% or more, preferably 70% or more, more preferably 80% or more, much more preferably 90% or more; preferably, five-hour biodegradation is required to attain a percent biodegradation of 50% or more, preferably 70% or more, more preferably 80% or more, much more preferably 90% or more; more preferably, four-hour biodegradation desirably attains a percent biodegradation of 50% or more, preferably 70% or more, more preferably 80% or more, much more preferably 90% or more; and more preferably, three-hour biodegradation desirably attains a percent biodegradation of 50% or more, preferably 70% or more, more preferably 80% or more, much more preferably 90% or more. The time necessary to biodegrade the derivative to 100% is controlled by determining the degrees of etherification or cross-linking.

In order to obtain a high strength of the gel, the percent biodegradation of the self-cross-linking alkyl cellulose derivative at eight hours is 40% or more, preferably 50% or more, more preferably 60% or more. The time necessary to biodegrade the derivative to 100% is controlled by determining the degree of etherification or cross-linking.

In the present invention, the self-cross-linking alkyl cellulose derivative irradiated with radioactive rays may be dried, and employed in the form of a solid or powder.

The method for drying the self-cross-linking alkyl cellulose derivative is not particularly limited, and the derivative may be dried by means of a known method, for example, through heating or vacuuming, to thereby control the moisture in the derivative to a desired level.

The water absorption ratio of the self-cross-linking alkyl cellulose derivative of the present invention is represented by the amount of distilled water which 1 g of the dried self-cross-linking alkyl cellulose derivative (gel) absorbs.

The water absorption ratio varies with the degree of gelation of the derivative, and the ratio is 30 g–1000 g/g-dried gel, preferably 100 g/g-dried gel or more, more preferably 200 g/g-dried gel or more.

The self-cross-linking alkyl cellulose derivative of the present invention exhibits water-absorbability, high gel strength, and/or biodegradability, in addition to the characteristics of the starting alkyl cellulose derivative. Therefore, the derivative can be employed for a variety of uses described in general publications or publications described in the "Background Art" of the present specification. In addition, the aforementioned characteristics allow the derivative to be used in products that must demonstrate a higher level of performance.

The self-cross-linking alkyl cellulose derivative which absorbs water 30 times or more its own weight can be suitably employed in medical products, cosmetic products, sanitary products, or agricultural water retention agents. The derivative is particularly suitable for diapers or sanitary napkins.

The self-cross-linking alkyl cellulose derivative having a gel compressive strength of 100 $g/cm^2$ or more is suitably employed in chromatography carriers, industrial materials, ground-improving agents, or soil-improving agents.

EXAMPLES

The present invention will next be described in more detail by way of Examples, which should not be construed as limiting the invention thereto.

Starting carboxyalkyl celluloses (product of Daicel Chem. Ind., Ltd.) employed in the Examples are as follows.

A: CMC, viscosity of 10 wt. % aqueous solution: 73 (mPa·s) at 20° C., average etherification degree: 1.27, percentage of carboxyl groups forming sodium chloride salts: 100%

B: CMC, viscosity of 10 wt. % aqueous solution: 161 (mPa·s) at 20° C., average etherification degree: 2.21, percentage of carboxyl groups forming sodium chloride salts: 100%

C: CMC, viscosity of 10 wt. % aqueous solution: 168 (mPa·s) at 20° C., average etherification degree: 0.86, percentage of carboxyl groups forming sodium chloride salts: 100%

D: CMC, viscosity of 10 wt. % aqueous solution: 250 (mPa·s) at 20° C., average etherification degree: 1.29, percentage of carboxyl groups forming sodium chloride salts: 100%

E: CMC, viscosity of 10 wt. % aqueous solution: 3670 (mPa·s) at 20° C., average etherification degree: 1.22, percentage of carboxyl groups forming sodium chloride salts: 100%

F: CMC, viscosity of 10 wt. % aqueous solution: 244 (mPa·s) at 20° C., average etherification degree: 1.32, percentage of carboxyl groups forming sodium chloride salts: 100%

G: carboxyethyl cellulose, viscosity of 10 wt. % aqueous solution: 200 (mPa·s) at 20° C., average etherification degree: 1.32, percentage of carboxyl groups forming sodium chloride salts: 100%

HPC1: hydroxypropyl cellulose, viscosity of 2 wt. % aqueous solution: 280 (mPa·s) at 20° C.

HPC2: hydroxypropyl cellulose, viscosity of 2 wt. % aqueous solution: 2,500 (mPa·s) at 20° C.

MC5: methyl cellulose, viscosity of 2 wt. % aqueous solution: 25 (mPa·s) at 20° C.

MC6: methyl cellulose, viscosity of 2 wt. % aqueous solution: 7,500 (mPa·s) at 20° C.

Example 1

Aqueous solutions each containing starting material F in an amount of 5, 10, 20, or 30 wt. % were irradiated with γ-rays.

The results are shown in FIG. 1. The x-axis of the graph shown in FIG. 1 represents the dose of γ-rays (unit: kGy), and the y-axis represents the gel fraction (wt. %) of CMC after irradiation.

Example 2

Aqueous solutions each containing one of starting materials A through E in an amount of 20 wt. % were irradiated with γ-rays.

Figure 2:
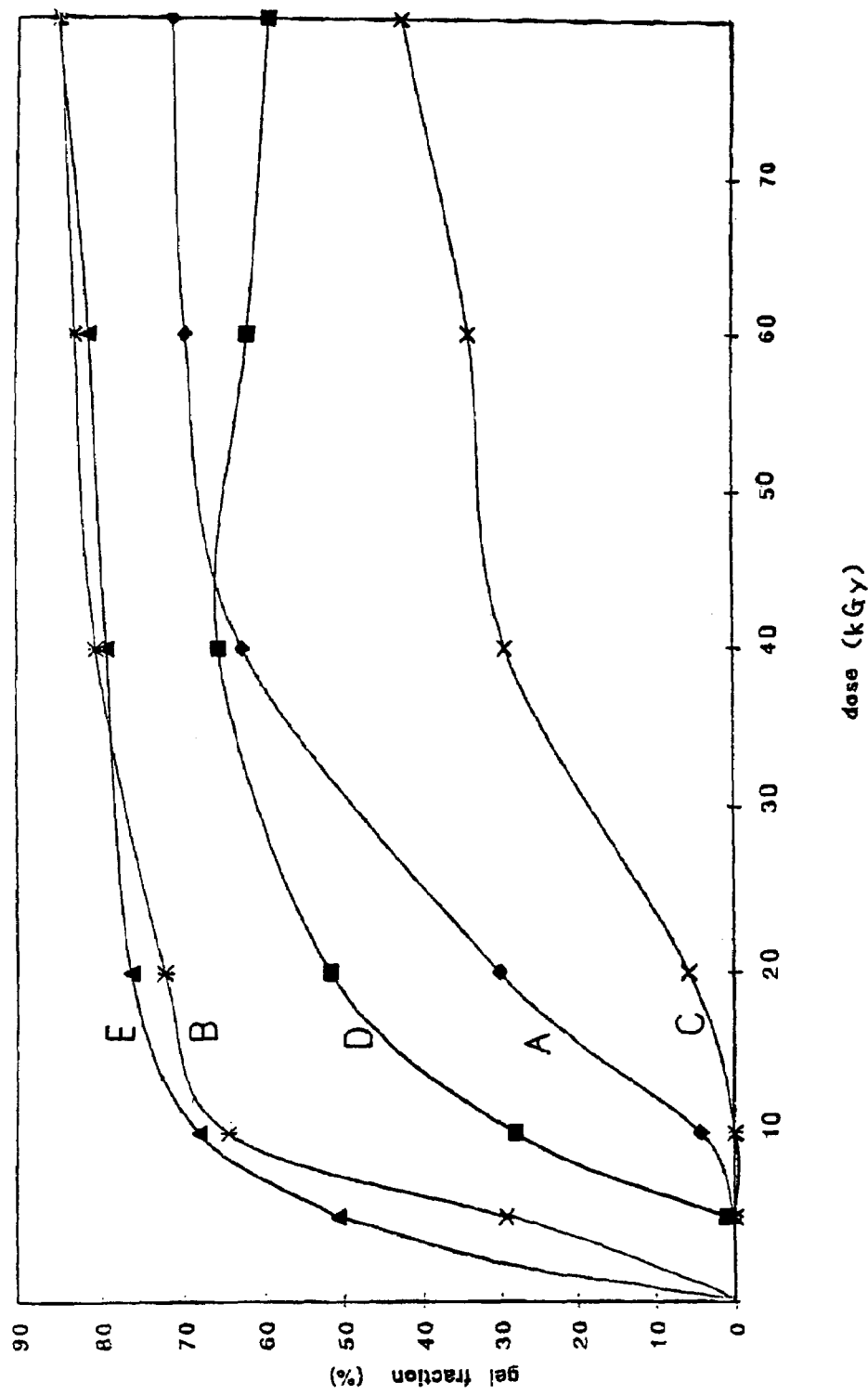
FIG. 2 is a graph obtained from the results of Example 2 and showing the relation between the irradiation dose and the gel fraction.

The results are shown in FIG. 2. The x-axis of the graph shown in FIG. 2 represents the dose of γ-rays (unit: kGy), and the y-axis represents the gel fraction (wt. %) of CMC after irradiation.

Example 3

Aqueous solutions each containing starting material F in an amount of 5, 10, 20, or 30 wt. % were irradiated with γ-rays. After completion of irradiation, the resultant CMC was dried, and the water absorption of the dried CMC was measured.

Figure 3:
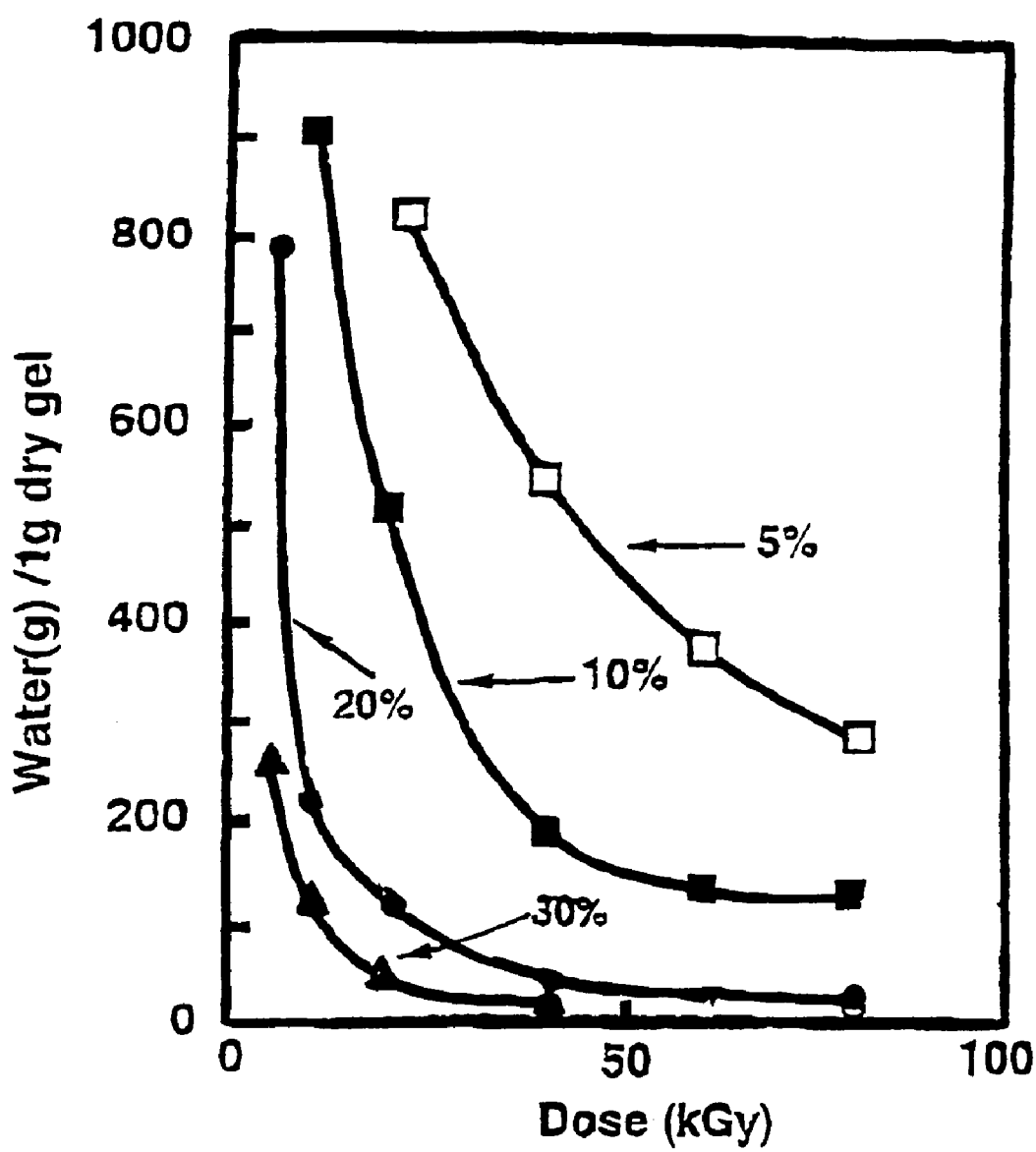
FIG. 3 is a graph obtained from the results of Example 3 and showing the relation between the irradiation dose and water absorption of dried products.

The results are shown in FIG. 3. The x-axis of the graph shown in FIG. 3 represents the dose of γ-rays (unit: kGy), and the y-axis represents the amount of water (g) absorbed in 1 g of the dried gel of the irradiated CMC.

Example 4

Aqueous solutions each containing starting material F in an amount of 20 or 30 wt. % were irradiated with γ-rays of 20 kGy.

Figure 4:
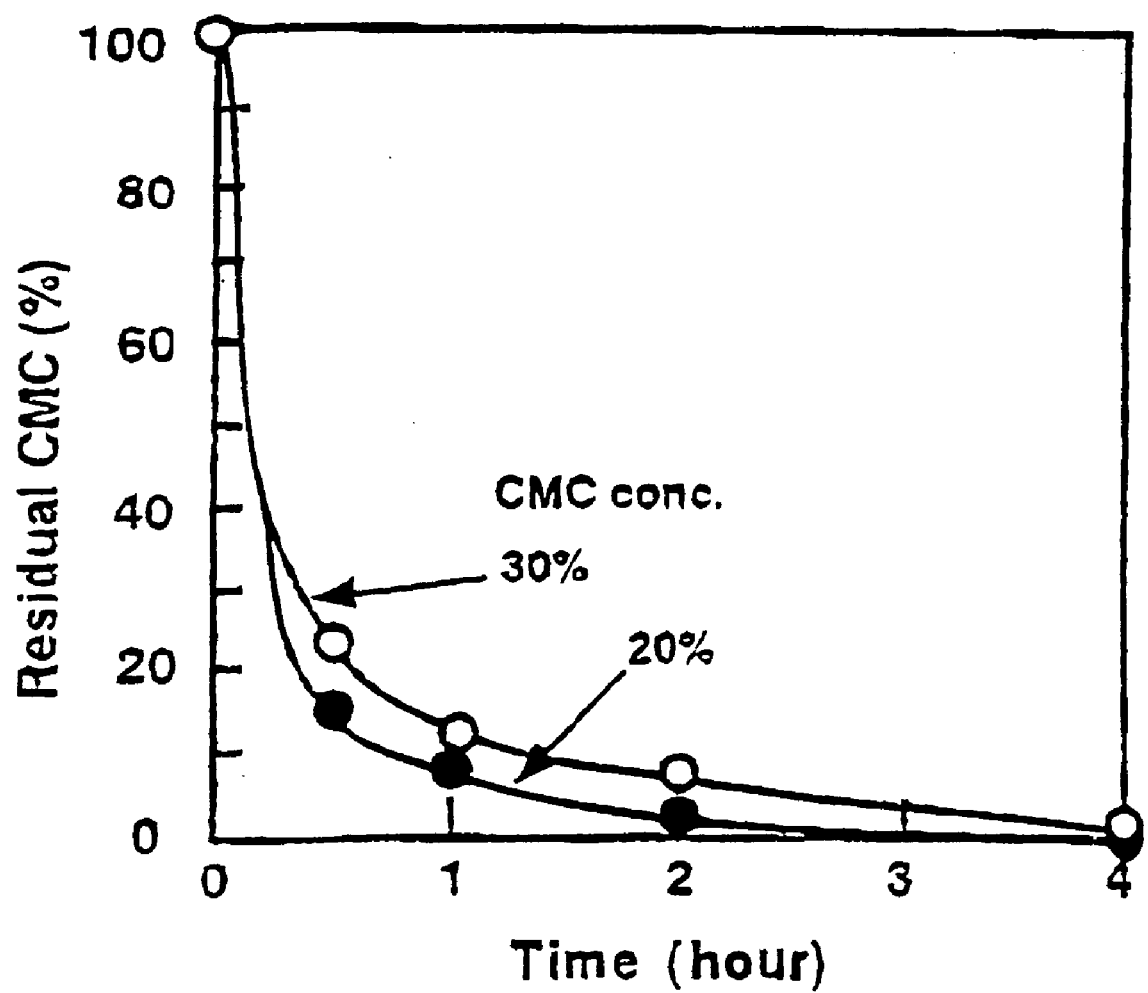
FIG. 4 is a graph obtained from the results of Example 4 and showing changes over time in percent biodegradation.

After completion of irradiation, the respective CMC solutions were subjected to biodegradation by use of cellulase. The percent biodegradation of each of the CMC solutions is shown in FIG. 4. The x-axis of the graph shown in FIG. 4 represents the biodegradation time (hours), and the y-axis represents the remaining CMC (%). The percent biodegradation is obtained by subtracting the remaining CMC (%) from 100%.

In the case in which an enzyme cellulase is employed, the percent biodegradation of CMC after irradiation is higher than that of the CMC before irradiation. Also, in the case in which a compost is employed, the percent biodegradation of the CMC after irradiation is higher than that of the CMC before irradiation.

Example 5

An aqueous solution of starting material G in an amount of 20 wt. % was irradiated with γ-rays.

Similar to the case of Example 1, the gel fraction of the resultant product increases as the dose of γ-rays increases.

Example 6

Aqueous solutions each containing HPC1, HPC2, MC5, or MC6 in an amount of 30 wt. % were irradiated with γ-rays.

Figure 5:
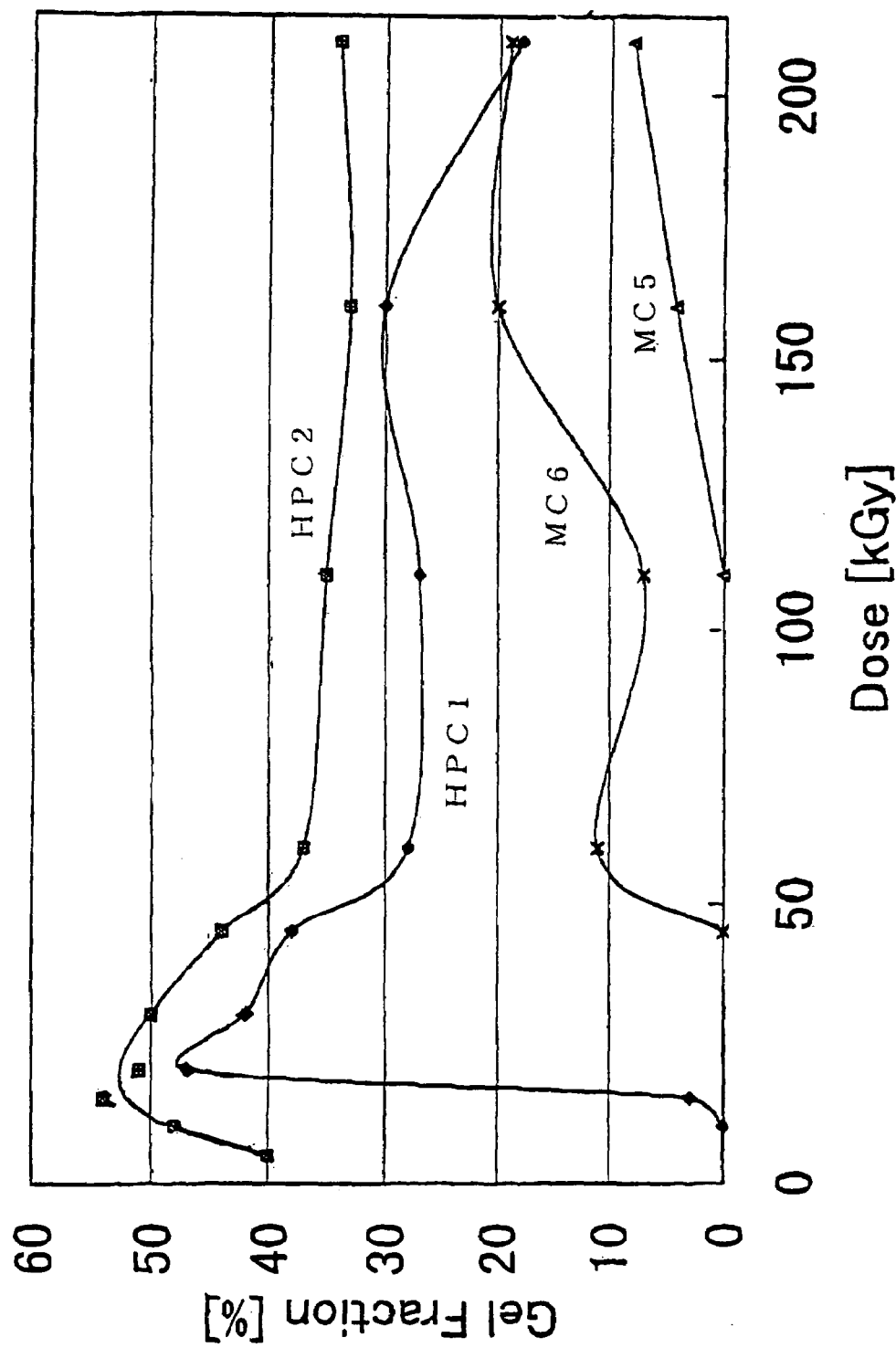
FIG. 5 is a graph obtained from the results of Example 6 and showing the relation between the irradiation dose and the gel fraction.

The results are shown in FIG. 5. The x-axis of the graph shown in FIG. 5 represents the dose of γ-rays (unit: kGy), and the y-axis represents the gel fraction (wt. %) of HPC1, HPC2, MC5, and MC6 after irradiation.

As is apparent from FIG. 5, each of HPC1 and HPC2 exhibits a peak of the gel fraction when the dose of γ-rays is 10–40 kGy, demonstrating achievement of satisfactory cross-linking.

In the meantime, MC6 is cross-linked when the dose of γ-rays is high, and MC5, which has a low polymerization degree, is cross-linked when the dose is higher.

Example 7

Aqueous solutions each containing HPC1 or HPC2 in an amount of 40 wt. % were irradiated with γ-rays.

Figure 6:
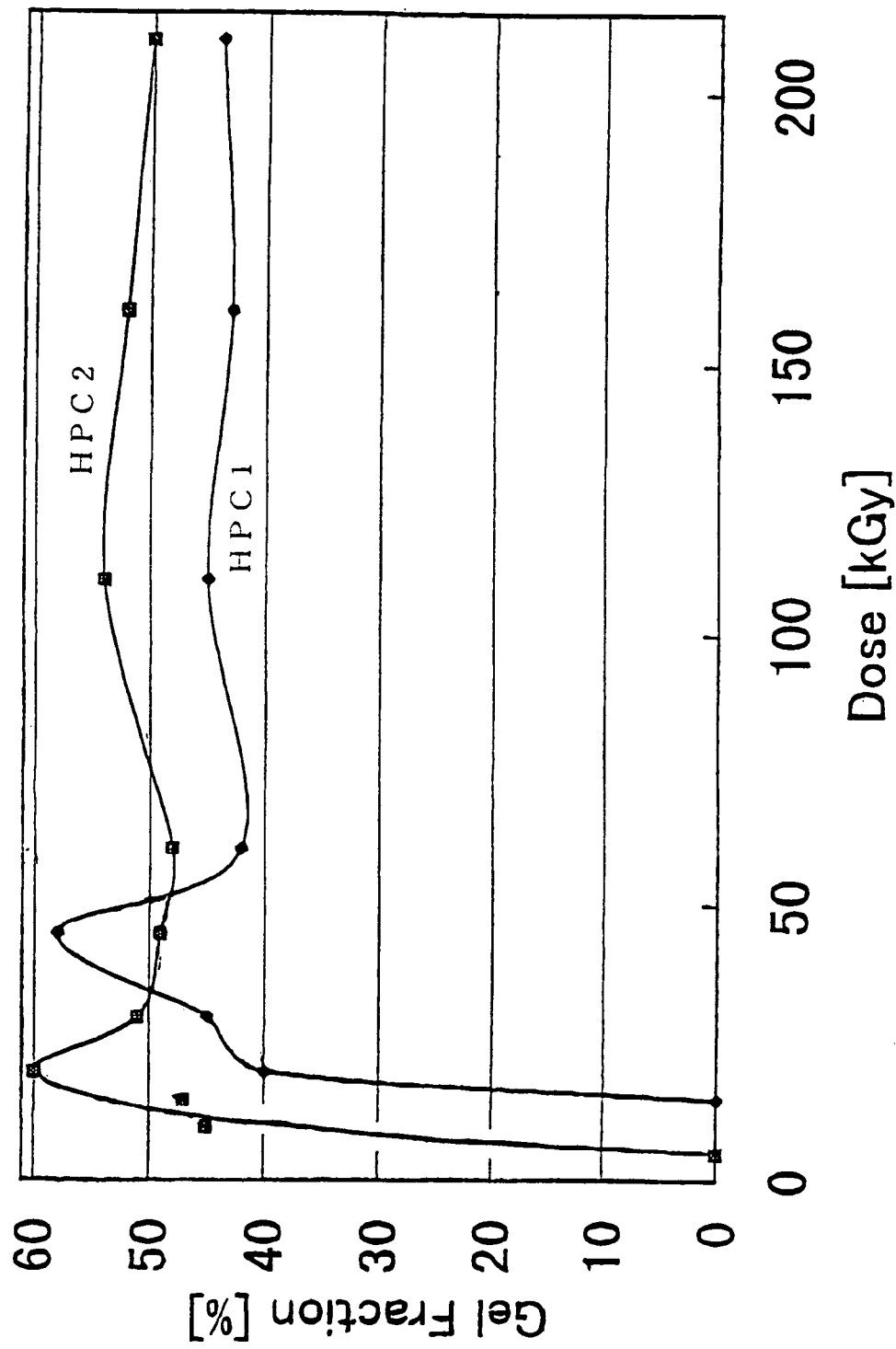
FIG. 6 is a graph obtained from the results of Example 7 and showing the relation between the irradiation dose and the gel fraction.

The results are shown in FIG. 6. The x-axis of the graph shown in FIG. 6 represents the dose of γ-rays (unit: kGy), and the y-axis represents the gel fraction (wt. %) of HPC1 and HPC2 after irradiation.

As is apparent from FIG. 6, the degree of cross-linking of the aqueous solution containing HPC in an amount of 40 wt. % is higher than that of the aqueous solution containing each of HPC in an amount of 30 wt. %.

According to the present invention, a self-cross-linking alkyl cellulose derivative is produced.

A water-absorbable resin or a gel of high strength can be produced depending on the type of starting alkyl cellulose derivative, the percentage of water during irradiation, or the dose of radioactive rays. In addition, by modifying such conditions, a biodegradable self-cross-linking alkyl cellulose derivative is produced.

We claim:

1. A self-cross-linked alkyl cellulose which is a radioactive ray-irradiated reaction product at a radiation dosage level of 0.1 to 300 kGy of a mixture at a dosage of 0.1 kGy to 300 kGy, the mixture comprising 100 parts by weight of an alkyl cellulose wherein the alkyl group has 1 to 3 carbon atoms, and at least a part of the alkyl group is substituted by a carboxyl group, and wherein the carboxyl group may be in the form of a salt, and 5 to 2,000 parts by weight of water.

2. A self-cross-linked alkyl cellulose according to claim 1, wherein when 0.2 g of the dried self-cross-linked alkyl cellulose is added to 10 ml of a buffered aqueous acetic acid solution having a pH of 4.5 containing 0.5 wt. % of cellulase and the resultant solution is allowed to stand at 40° C. for eight hours, the percent biodegradation of the self-cross-linked alkyl cellulose is 50% or more.

3. A self-cross-linked alkyl cellulose according to claim 1, wherein the self-cross-linked alkyl cellulose absorbs 30 times or more its weight of distilled water.

4. A self-cross-linked alkyl cellulose according to claim 1, in the form of a gel having a compressive strength of 100 g/cm$^2$ or more.

5. A self-cross-linked alkyl cellulose which is a radioactive ray-irradiated reaction product at a radiation dosage level of 0.1 to 300 kGy of a mixture at a dosage of 0.1 kGy to 300 kGy, the mixture comprising 100 parts by weight of an alkyl cellulose, and 5 to 233 parts by weight of water, .wherein the alkyl cellulose comprises:
  (i) an alkyl cellulose having a C1–C3 alkyl group, or
  (ii) an alkyl cellulose having an alkyl group which is selected from the group consisting of (a) a hydroxyisopropyl group, (b) a hydroxyl n-propyl group, (c) a polyoxyalkylene ether-substituted hydroxyisopropyl group which is the reaction product of a hydroxyisopropyl group with 1 to 10 molecules of ethylene oxide or propylene oxide, and (d) a polyoxyalkylene ether-substituted hydroxyl-n-propyl group which is the reaction product of a hydroxyl-n-propyl group with 1 to 10 molecules of ethylene oxide or propylene oxide.

6. A self-cross-linked alkyl cellulose according to claim 5, wherein when 0.2 g of the dried self-cross-linked alkyl cellulose is added to 10 ml of a buffered aqueous acetic acid solution having a pH of 4.5 containing 0.5 wt. % of cellulase and the resultant solution is allowed to stand at 40° C. for eight hours, the percent biodegradation of the self-cross-linked alkyl cellulose is 50% or more.

7. A self-cross-linked alkyl cellulose according to claim 5, wherein the self-cross-linked alkyl cellulose absorbs 30 times or more its weight of distilled water.

8. A self-cross-linked alkyl cellulose according to claim 5, in the form of a gel having a compressive strength of 100 g/cm$^2$ or more.

9. A self-cross-linked alkyl cellulose according to claim 1. wherein the alkyl cellulose has the average polymerization degree of 50 to 1000.

10. A self-cross-linked alkyl cellulose according to claim 1, wherein the alkyl cellulose has the average etherification degree of 0.8 to 3.

11. A self-cross-linked alkyl cellulose according to claim 1, wherein the self-cross-linked alkyl cellulose has a gel fraction of 0.1 to 30%.

12. A self-cross-linked alkyl cellulose according to claim 1, wherein the self-cross-linked alkyl cellulose has a gel fraction of 30% or more.

13. A self-cross-linked alkyl cellulose according to claim 5, wherein the alkyl cellulose has the average polymerization degree of 50 to 1000.

14. A self-cross-linked alkyl cellulose according to claim 5, wherein the alkyl cellulose has the average etherification degree of 0.8 to 3.

15. A self-cross-linked alkyl cellulose according to claim 5, wherein the self-cross-linked alkyl cellulose has a gel fraction of 30% or more.

* * * * *

UNITED STATES PATENT AND TRADEMARK OFFICE
CERTIFICATE OF CORRECTION

PATENT NO. : 7,208,593 B2
APPLICATION NO. : 11/062565
DATED : April 24, 2007
INVENTOR(S) : Yoshii et al.

It is certified that error appears in the above-identified patent and that said Letters Patent is hereby corrected as shown below:

Column 10, line 35, after "product" insert --of a mixture--;

lines 36-37, delete "of a mixture at a dosage of 0.1 kGy to 300 kGY";

line 56, after "product" insert --of a mixture--; and lines 57-58, delete "of a mixture at a dosage of 0.1 kGy to 300 kGY".

Signed and Sealed this

Tenth Day of July, 2007

JON W. DUDAS
*Director of the United States Patent and Trademark Office*